(12) United States Patent
Zhang et al.

(10) Patent No.: US 8,469,933 B2
(45) Date of Patent: Jun. 25, 2013

(54) PUMP ACTIVATED PINCH CLAMP

(75) Inventors: Mei Zhang, Sharon, MA (US); Chaoyoung Lee, Weston, MA (US)

(73) Assignee: Zyno Medical LLC, Natick, MA (US)

( * ) Notice: Subject to any disclaimer, the term of this patent is extended or adjusted under 35 U.S.C. 154(b) by 29 days.

(21) Appl. No.: 13/051,306

(22) Filed: Mar. 18, 2011

(65) Prior Publication Data
US 2012/0238991 A1    Sep. 20, 2012

(51) Int. Cl.
*A61M 5/00*    (2006.01)
(52) U.S. Cl.
USPC .............................. 604/250; 604/151; 251/10
(58) Field of Classification Search
USPC ..................... 604/151, 250; 251/10
See application file for complete search history.

(56) References Cited

U.S. PATENT DOCUMENTS

| | | | |
|---|---|---|---|
| 2,889,848 A | 6/1959 | Redmer | |
| 4,071,930 A | 2/1978 | Tanaka | |
| 4,077,601 A | 3/1978 | Dick | |
| 4,248,401 A | 2/1981 | Mittleman | |
| 4,453,295 A | 6/1984 | Laszczower | |
| 4,586,691 A | 5/1986 | Kozlow | |
| 4,588,160 A | 5/1986 | Flynn | |
| 4,866,818 A | 9/1989 | Thompson | |
| 5,232,193 A | 8/1993 | Skakoon | |
| 5,238,218 A | 8/1993 | Mackal | |
| 5,290,239 A | 3/1994 | Classey | |
| 5,300,044 A | 4/1994 | Classey | |
| 5,401,256 A | 3/1995 | Stone | |
| 5,437,635 A | 8/1995 | Fields | |
| D362,062 S | 9/1995 | Botts | |
| 5,453,098 A | 9/1995 | Botts | |
| 5,810,323 A | 9/1998 | Winterer | |
| 5,967,484 A | 10/1999 | Morris | |
| 6,234,448 B1 | 5/2001 | Porat | |
| 6,261,262 B1 | 7/2001 | Briggs | |
| 6,364,279 B1 | 4/2002 | Neftel | |
| 6,629,955 B2 | 10/2003 | Morris | |
| 6,742,760 B2 | 6/2004 | Blickhan | |
| 6,942,473 B2 | 9/2005 | Abrahamson | |
| 7,124,996 B2 | 10/2006 | Clarke | |
| 7,234,677 B2 | 6/2007 | Zerfas | |
| 7,303,175 B2 | 12/2007 | Smith | |
| 7,419,133 B2 | 9/2008 | Clarke | |
| 2002/0165503 A1 | 11/2002 | Morris | |
| 2005/0020978 A1 | 1/2005 | Vollenweider | |
| 2006/0071187 A1 | 4/2006 | Aulicino | |
| 2006/0081797 A1 | 4/2006 | Zerfas | |
| 2007/0252096 A1 | 11/2007 | Zerfas | |
| 2008/0051731 A1* | 2/2008 | Schweikert et al. | 604/250 |
| 2009/0264857 A1* | 10/2009 | Susi | 604/506 |
| 2012/0101437 A1 | 4/2012 | Gagliardoni | |

\* cited by examiner

*Primary Examiner* — Emily Schmidt
(74) *Attorney, Agent, or Firm* — James Marc Leas

(57) ABSTRACT

A system for controlling flow of a fluid in a tube with a controlling device includes a pinch clamp. The pinch clamp has a first leg, a second leg, a connecting region there between, a pinching region, and a first part of a quick release connector. The first leg and the second leg are both connected to the connecting region. Whether the pinching region is in an open position or in a closed position is determined by spacing between the first leg and the second leg. The first leg includes the first part of the quick release connector. The first part of the quick release connector includes an element for quickly mounting the pinch clamp to the controlling device and for quickly dismounting the pinch clamp from the controlling device.

41 Claims, 19 Drawing Sheets

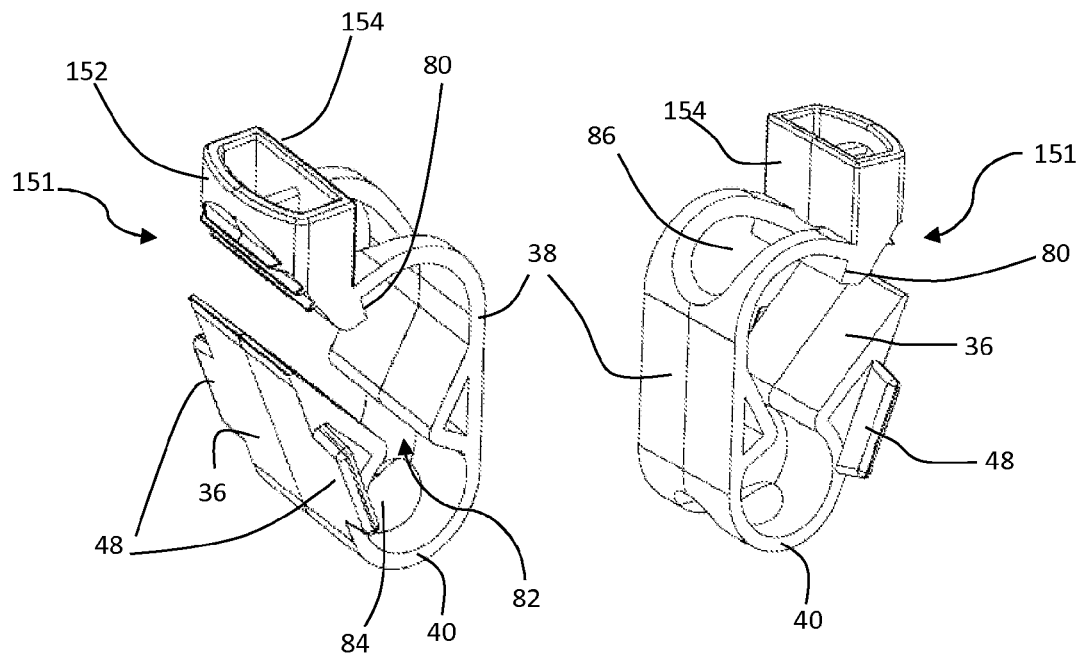
FIG. 11a
FIG. 11b
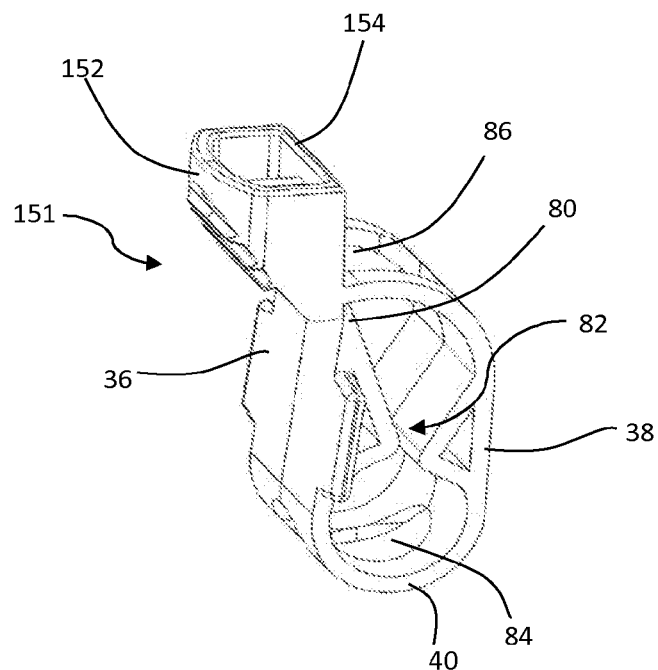
FIG. 11c

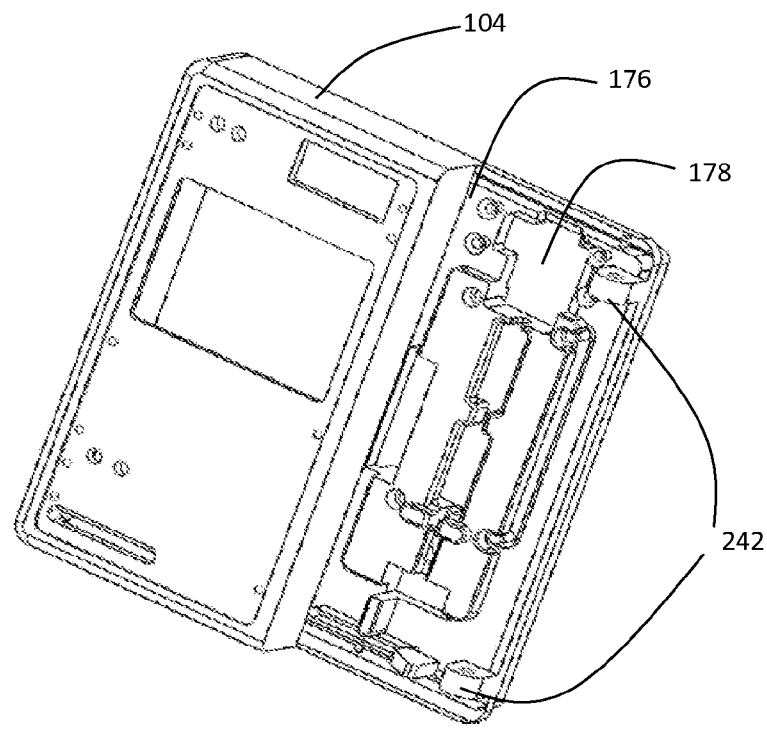
FIG. 13c
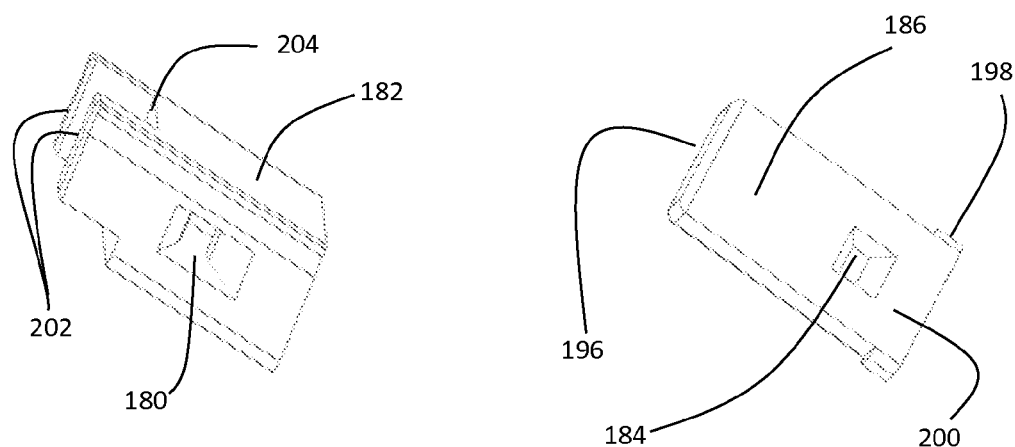
FIG. 13d
FIG. 13e

US 8,469,933 B2

PUMP ACTIVATED PINCH CLAMP

PRIORITY

This application claims the benefit of U.S. Provisional Patent Application 61/316,802, filed Mar. 23, 2010, "Pump Activated Pinch Clamp," incorporated herein by reference.

FIELD

This patent application generally relates to a system for pumping fluids. More particularly it relates to a tube pinch clamp for use in pump. More particularly it relates to a tube pinch clamp for use in an infusion pump.

BACKGROUND

Infusion pumps have been used to provide a fluid containing medicine to a patient in a controlled manner. The fluid may be supplied in a bag with tubing extending. The tubing is operated on by the pump to provide a specified flow rate. In designing the pump schemes have been implemented to prevent continued flow of the fluid when the pump is opened or when tubing is removed from the pump so that the patient does not experience unwanted fluid pressure or receive an unwanted quantity of the fluid. A better system for automatically controlling fluid flow in the tubing has been needed, and such a system is provided in this patent application.

SUMMARY

One aspect of the present patent application is a system for controlling flow of a fluid in a tube with a controlling device. The system includes a pinch clamp. The pinch clamp has a first leg, a second leg, a connecting region there between, a pinching region, and a first part of a quick release connector. The first leg and the second leg are both connected to the connecting region. Whether the pinching region is in an open position or in a closed position is determined by spacing between the first leg and the second leg. The first leg includes the first part of the quick release connector. The first part of the quick release connector includes an element for quickly mounting the pinch clamp to the controlling device and for quickly dismounting the pinch clamp from the controlling device.

Another aspect of the present patent application is a system that includes a pinch clamp, a tube for providing a fluid, and a control housing. The pinch clamp is mounted on the tube for controlling flow of the fluid. The tube and the pinch clamp are for fitting in the control housing. The pinch clamp has a closed position and an open position, wherein when the pinch clamp is in the closed position flow of the fluid is prevented and when the pinch clamp is in the open position the fluid can flow in the tube. The control housing includes a first force applying device and a second force applying device. The first force applying device automatically forces the pinch clamp into the closed position and the second force applying device counters the first force applying device and automatically forces the pinch clamp into the open position. The second force applying device is different from the first force applying device.

Another aspect of the present patent application is a method of operating a pump for pumping a fluid. The method includes providing the pump. The pump includes a pump housing, a door, and a clamp holding device. The clamp holding device includes a first forcing element and the door includes a second forcing element. The method also includes providing a tube and a clamp. The clamp has a first leg and a second leg. The clamp has an open position and a closed position. When the clamp is in the open position the clamp does not prevent fluid flow and when the clamp is in the closed position fluid cannot flow. The method also includes inserting the first leg into the clamp holding device. When the clamp holding device holds the first leg and when the door is open the first forcing element acts to force the clamp to be in a closed position. The method also includes closing the door, wherein the door closing activates the second forcing element. The second forcing element acts to force the clamp to be in the open position.

Another aspect of the present patent application is a system that includes a pinch clamp and a clamp holding device. The pinch clamp has an open position and a closed position. The pinch clamp has a first leg and a second leg. The first leg includes a first part of a quick release connector and the clamp holding device includes a second part of the quick release connector. The second part of the quick release connector is for holding the first part of the quick release connector.

BRIEF DESCRIPTION OF THE DRAWINGS

FIG. 1b is a three dimensional view of a pump activated pinch clamp to be inserted into the clamp holding device of the infusion pump of FIG. 1a;

FIG. 2a is an enlarged three dimensional view of the clamp holding device of FIG. 1a;

FIG. 2b is an enlarged three dimensional view of the pump activated pinch clamp of FIG. 1b;

FIG. 5a is another enlarged three dimensional view of the clamp holding device and the back cover of FIGS. 1a and 2a;

FIG. 5b is an enlarged three dimensional view of the main body of the clamp holding device of FIG. 5a;

FIG. 6a is an enlarged three dimensional view of a spring loaded block portion of the clamp holding device of FIG. 5a;

FIG. 6b is an enlarged three dimensional view of a spring loaded block with its springs as it fits into the main body of the clamp holding device of FIG. 5a;

FIG. 7b is a three dimensional view of the infusion pump of FIG. 7a;

FIGS. 11a and 11b are three dimensional views of another embodiment of a pump activated pinch clamp in the open position;

FIG. 11c is a three dimensional views of the embodiment of a pump activated pinch clamp of FIGS. 11a-11b in the closed position;

FIG. 13c is a three dimensional view of the pump housing front panel showing the opening in which to install the clamp holder and components for closing the pump activated pinch clamp of FIGS. 11a-11c when the pump door is opened;

FIG. 13d is a three dimensional view of a clamp block, one of the components for closing the pump activated pinch clamp of FIGS. 11a-11c when the pump door is opened;

FIG. 13e is a three dimensional view of a straight block, a components that facilitates opening the pump activated pinch clamp of FIGS. 11a-11c when the pump door is closed;

FIG. 14b is a three dimensional view of a back view of the infusion pump showing the back of the spring housing of FIG. 14a;

FIG. 15b is a three dimensional view of a pump door showing mounting holes for installation of the door block of FIG. 15a;

FIG. 17b is a three dimensional view of another embodiment of a clamp holder with a slot to install a hall sensor for detecting presence and position of the pump activated pinch clamp of FIG. 17a.

DETAILED DESCRIPTION

Figure 1A:
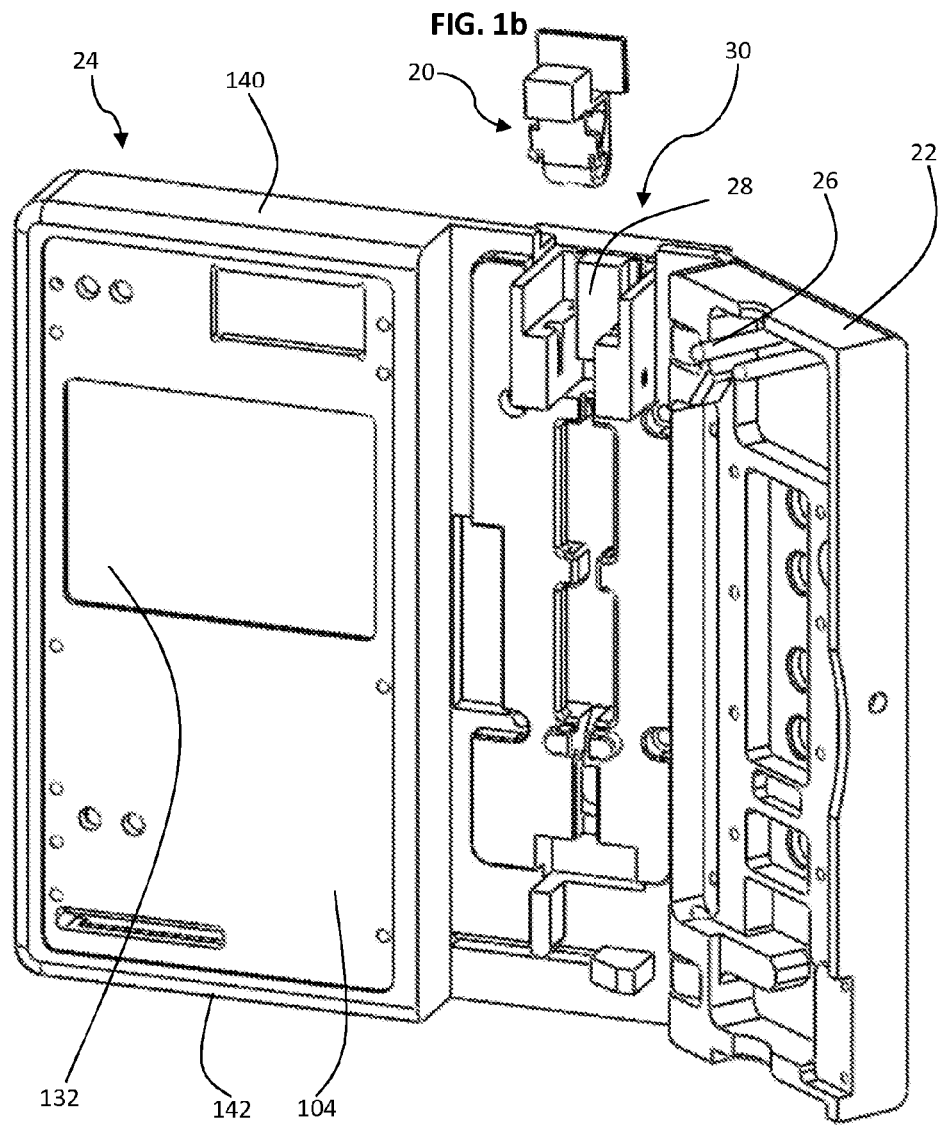
FIG. 1a is a three dimensional view of the front portion of an infusion pump housing with its door open.

The present applicants designed pump activated pinch clamp 20, 20' for allowing or preventing flow of a fluid in flexible tube 21, as shown in FIGS. 1a-1d. In addition to having capability of being operated with human fingers, pump activated pinch clamp 20, 20' is also capable of being automatically operated by opening or closing door 22 of a device, such as infusion pump 24, as shown in FIG. 1a.

In one embodiment, when door 22 of infusion pump 24 is closed, a device, such as pins 26, in pump door 22 automatically force pump activated pinch clamp 20, 20' into its open position, allowing free flow of the fluid in the tube. Then, when door 22 of infusion pump 24 is opened, another device, such as spring loaded block 28 of clamp holding device 30, automatically forces pump activated pinch clamp 20, 20' into its closed position, preventing flow of the fluid.

Pump activated pinch clamp 20, 20' remains in the closed position while door 22 is open and when the tube to which pump activated pinch clamp 20, 20' is connected is removed from infusion pump 24. In this embodiment, initial insertion of the tube with its pump activated pinch clamp 20, 20' into infusion pump 24 automatically forces pump activated pinch clamp 20, 20' into its closed position if it was not already in that position.

Figure 2A:
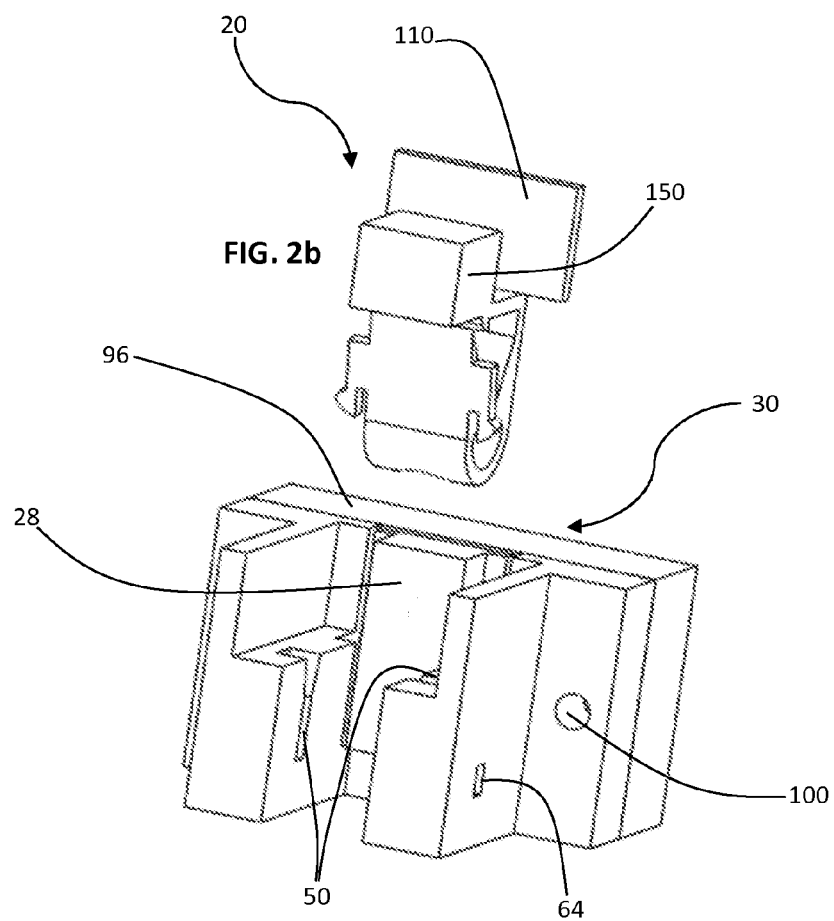
Figure 3A:
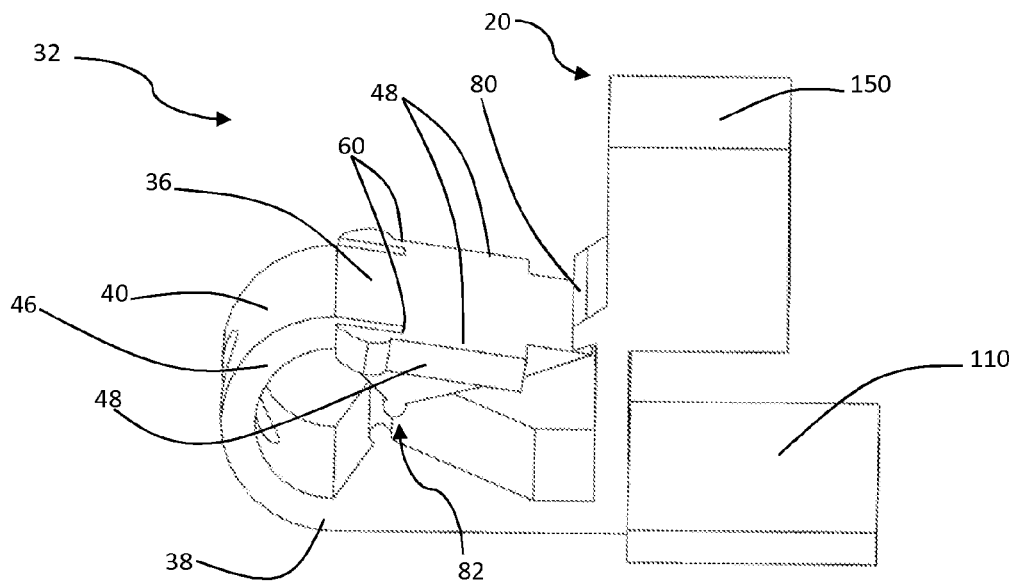
FIG. 3a is another three dimensional view of the pump activated pinch clamp of FIGS. 1b and 2b showing it in the closed position.
Figure 3B:
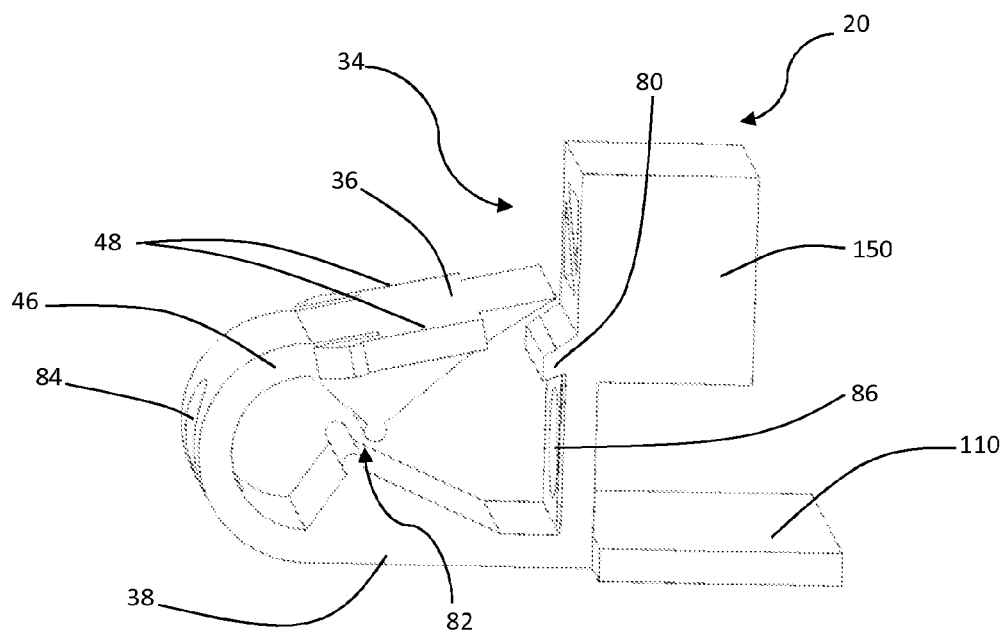
FIG. 3b is another three dimensional view of the pump activated pinch clamp of FIGS. 1b and 2b showing it in the open position.

In one embodiment, pump activated pinch clamp 20 is inserted into clamp holding device 30 in infusion pump 24, as shown in enlarged view in FIGS. 2a, 2b. In this embodiment, pump activated pinch clamp 20 has a closed position 32, as shown in FIG. 3a and an open position 34, as shown in FIG. 3b. Pump activated pinch clamp 20 has a shorter leg 36, a longer leg 38, and a connecting region 40 there between. Connecting region 40 has edge 46, and first leg 36 includes a first part of a quick release connector, such as wing region 48, that extends beyond edge 46.

Figure 5A:
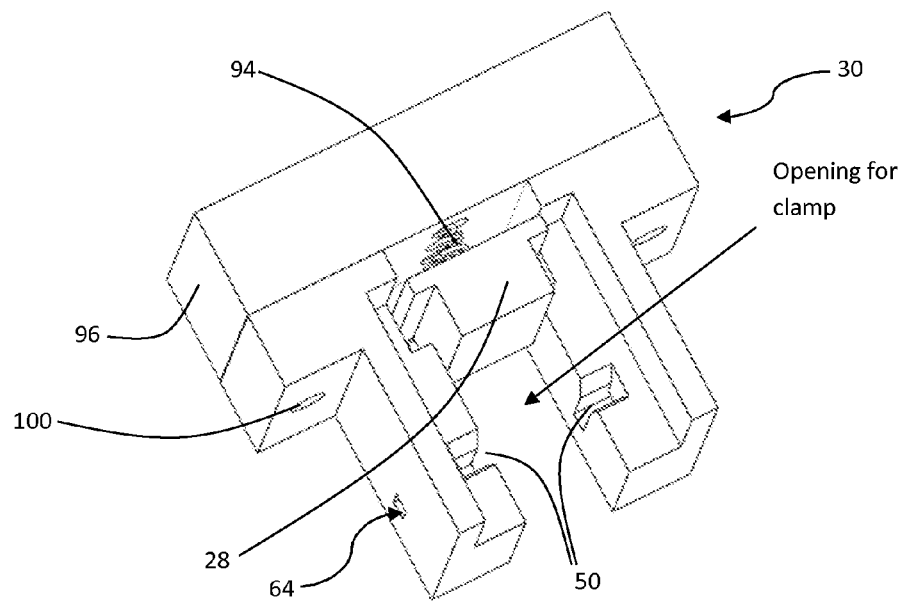
Figure 5B:
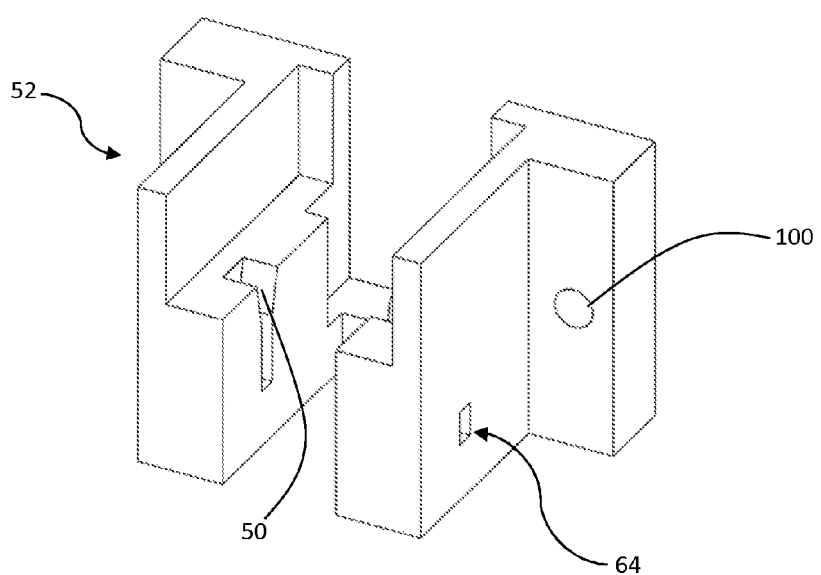
Figure 6A:
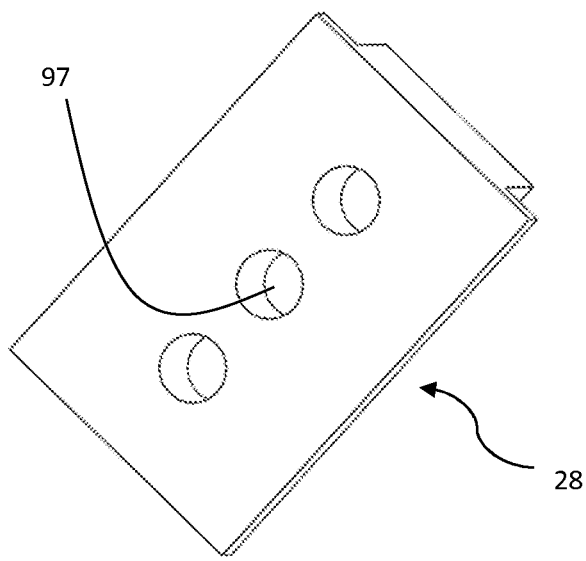
Figure 6B:
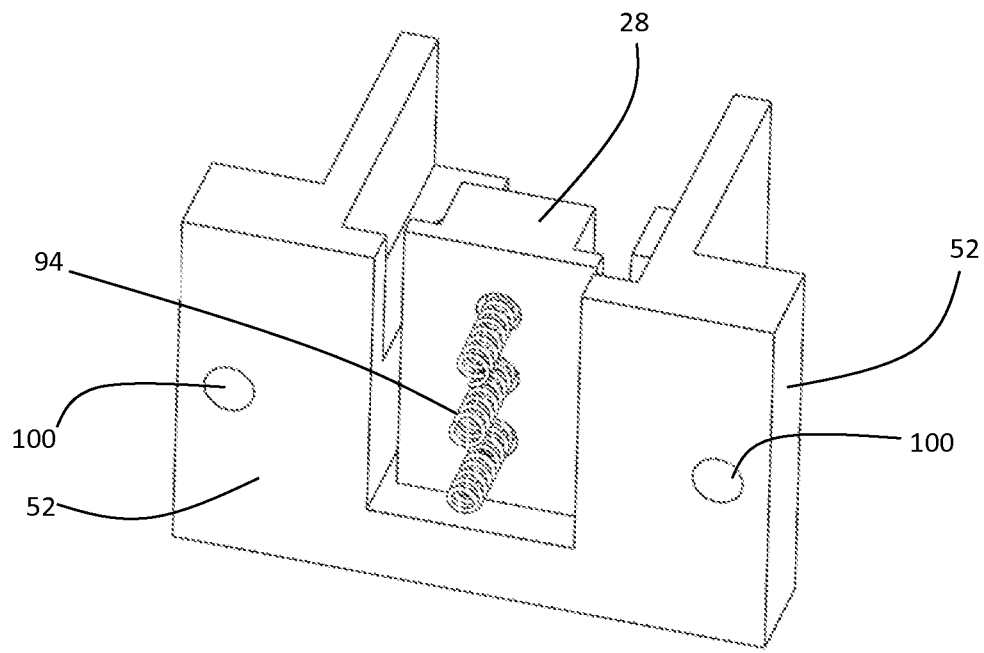

The extension beyond edge 46 of connecting region 40 allows wing region 48 to slide into a second part of the quick release connector, such as slot 50 of main body 52 of clamp holding device 30, as shown in FIG. 5b. In one embodiment, wing region 48 extends on each side of shorter leg 36, as shown in FIGS. 3a, 3b. Main body 52 of clamp holding device 30 has slot 50 on each side, as shown in FIGS. 2a and 5b, into which wing region 48 extends for holding shorter leg 36 in a fixed position. Slot 50 can be tapered as shown, allowing easy insertion of wing region 48 of shorter leg 36. In one variation, a single wing region on one side of the first leg may be used. Wing region 48 allows clamp holding device 30 to hold shorter leg 36 in a fixed position while longer leg 38 can freely move. Wing region 36 and slot 50 allow shorter leg 36 of pump activated pinch clamp 20 to be quickly connected to and disconnected from clamp holding device 30.

Position of longer leg 38 determines whether pump activated pinch clamp 20 is in open position 34 or in closed position 32 when shorter leg 36 of pump activated pinch clamp 20 is in clamp holding device 30. Though in FIGS. 3a, 3b, shorter leg 36 has wing region 48, the roles can be reversed so longer leg 38 has the wing region and shorter leg 36 is free to move.

Figure 4:
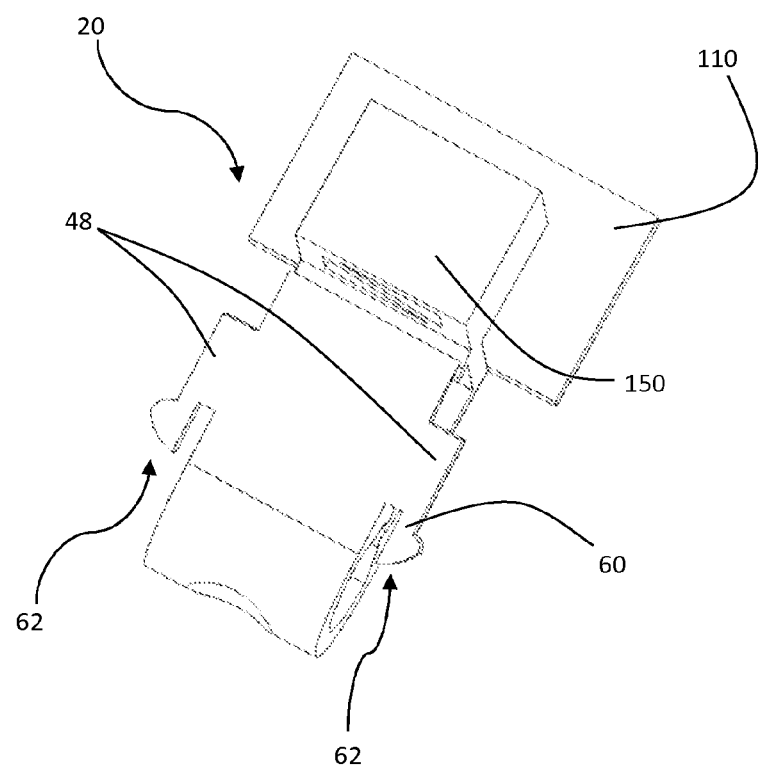
FIG. 4 is another three dimensional view of the pump activated pinch clamp of FIGS. 1b and 2b.

In one embodiment extensions 60 and quick release latching elements 62 are provided on each wing region 48, as shown in FIG. 4. Clamp holding device 30 has hole 64 into which quick release latching element 62 falls when quick release latching element 62 reaches hole 64, as shown in FIGS. 5a, 5b, securing pump activated pinch clamp 20 in place while making a clicking sound. The sound indicates to the user that pump activated pinch clamp 20 was properly inserted in clamp holding device 30. With the rounded shape of quick release latching element 62 shown in FIG. 4 pump activated pinch clamp 20 can be removed by pulling on pump activated pinch clamp 20. Alternatively, a shape to provide a latch can be used for the quick release latching element 62, such as flats, and a corresponding mechanism provided on clamp holding device 30 to allow for pressing extensions 60 toward each other to release the latch. Size of rounded quick release latching element 62 can be set smaller to make removal easier while still providing an identifiable sound when pump activated pinch clamp 20 is inserted. Other shapes and sizes for quick release latching element 62 and for hole 64 in clamp holding device 30 can also be used to make the removal easier or harder.

Figure 9:
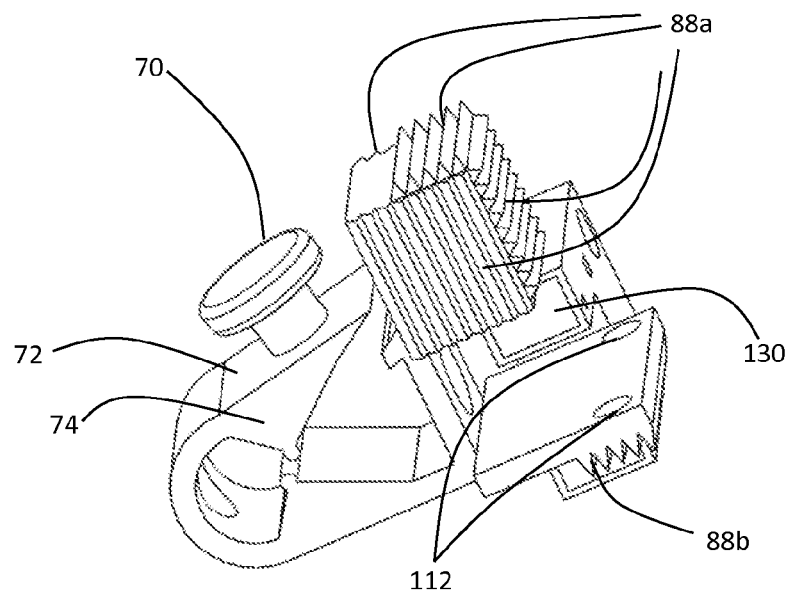
FIG. 9 is a three dimensional view of another embodiment of a pump activated pinch clamp.

In another embodiment, wing region 48 is replaced by a capturing member, such as button shaped protrusion 70 that extends perpendicular to surface 72 of first leg 74, as shown in FIG. 9. In this embodiment, the quick release connector is button shaped protrusion 70 that can slide into a corresponding slot in a clamp holding device for holding first leg 74 in a fixed position. Other shapes for the quick release connector can also be used.

As with prior art pinch clamps long in use for control by human fingers, pump activated pinch clamp 20 in this embodiment is a normally open type formed by injection molding a plastic material. Various plastics can be used, such as acetal, polyoxymethylene, polyester, and polypropylene. Other plastics can also be used. Pump activated pinch clamp 20 also includes latch 80 that holds pump activated pinch clamp 20 in its closed position, as shown in FIGS. 3a, 3b. Pump activated pinch clamp 20 also includes curved connecting region 40 where shorter leg 36 and longer leg 38 join. Curved connecting region 40 provides a built in spring that automatically opens pump activated pinch clamp 20 when pump activated pinch clamp 20 is delatched. Pump activated pinch clamp 20 also has pinching region 82 which pinches the tube when pump activated pinch clamp 20 is in closed position. Pump activated pinch clamp 20 also has openings 84, 86 through which the tube extends. Opening 84 for the tube extends through curved region 40. Opening 86 for the tube extends through a portion of longer leg 38 that bends toward shorter leg 36 for latch 80. Pinching region 82 is between openings 84 and 86. Rough surfaces 88a, 88b are also provided on surfaces of leg 38 used for pinching with fingers, as shown in FIG. 9. Other rough surfaces can be provided on shorter leg 36.

In one embodiment a first force applying device, such as spring loaded block 28 shown in FIGS. 5a, 6a-6b, and 7a automatically acts on longer leg 38 of pump activated pinch clamp 20 to force it toward shorter leg 36, closing pump activated pinch clamp 20 and latching its two legs 36, 38 together. Springs 94 between spring loaded block 28 and back cover 96, shown in more detail in FIGS. 5a, 6b, 7a, and 10 provide the force. Spring loaded block 28 can include blind holes 97 and back cover 96 can include blind holes 98 to act as catchment for springs 94, as shown in FIG. 8. Back cover 96 is connected to clamp holding device 30 with connectors, such as screws that extend through clearance holes 100 in clamp holding device. The same screws extend through clearance holes 102 in back cover 96 connecting both to pump housing 104, as shown in FIGS. 2a 7b, and 8.

Figure 7A:
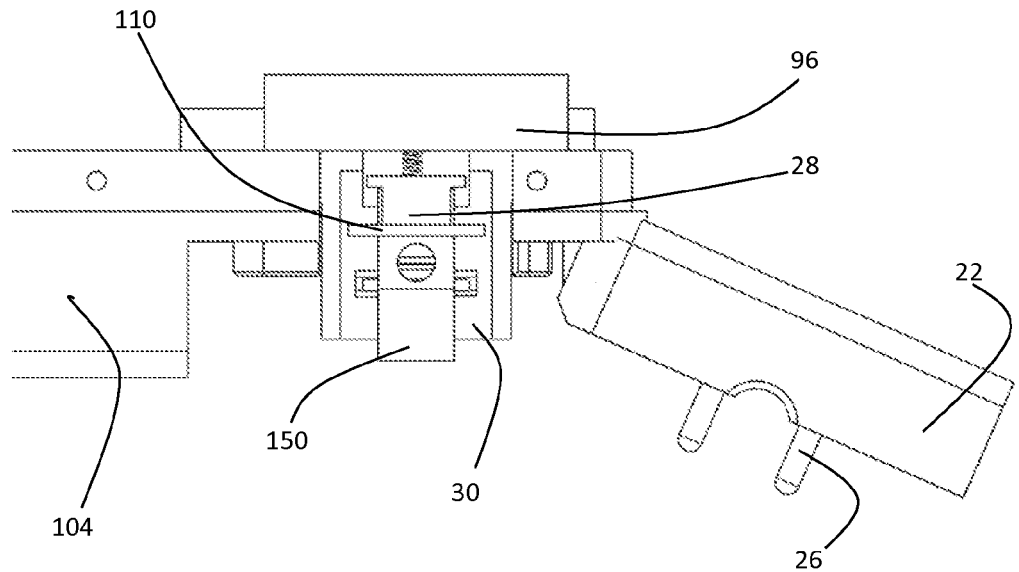
FIG. 7a is a top view of part of an infusion pump housing with its door open showing details of the clamp holding device with its spring loaded block and clamp showing how pins on the door of the infusion pump cause the clamp latch to be released when the door closes, opening the clamp, and pushing back the spring loaded block.
Figure 7B:
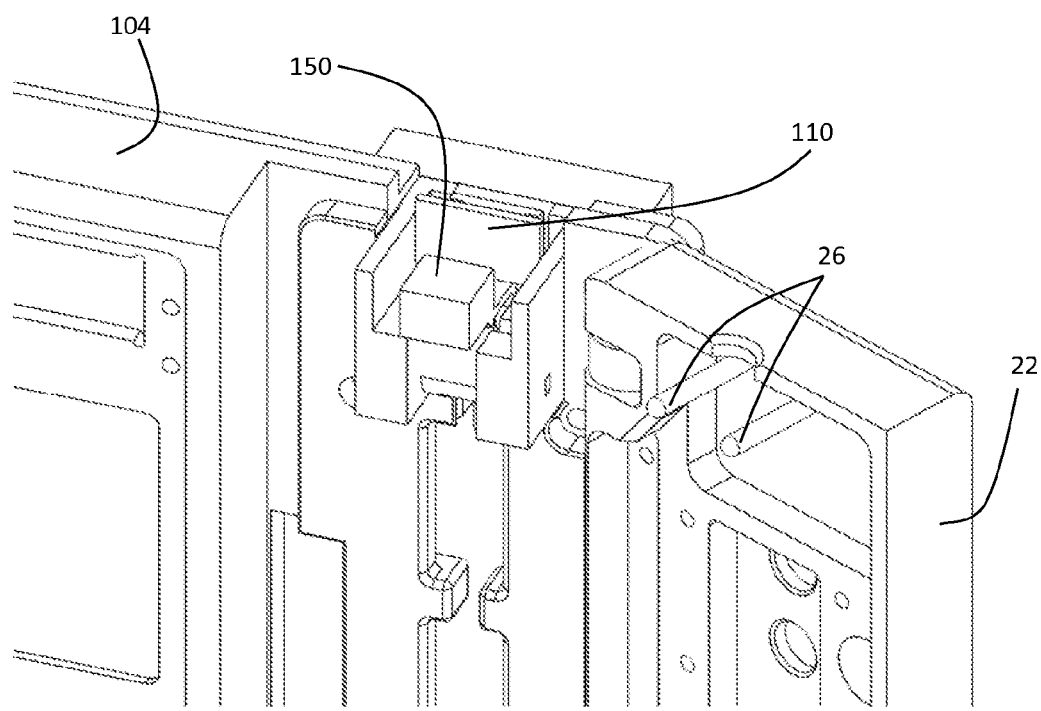
Figure 8:
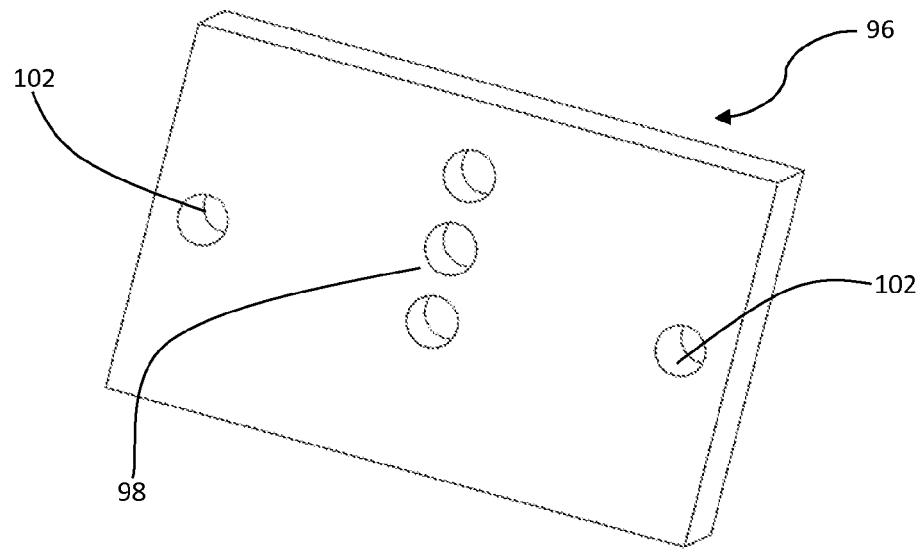
FIG. 8 is a three dimensional view of the back cover of the clamp holding device showing the screw clearance hole and the back cover spring encatchment.

When pump door 22 is open, no force counters action of this spring loaded block 28, so even if pump activated pinch clamp 20 is open when inserted into the clamp holding device 30, as shown in FIGS. 5a and 7a, action of the spring loaded block 28 will immediately cause pump activated pinch clamp 20 to close when it is inserted in slot 50 in clamp holding device 30.

When pump door 22 is closed, a force provided by pins 26 acts to push tab 110 on longer leg 38, which tilts longer leg 38, opening latch 80. The force of pins 26 also then pushes back longer leg 38, opening pump activated pinch clamp 20, as shown in FIGS. 7a-7b. Force of pins 26 acting through tab 110 counteracts the force of spring loaded block 28 and pushes spring loaded block 28 back toward back cover 96, compressing springs 94. While two pins 26 are shown, a single pin or three or more pins can be used. Recess 112 can be provided in tab 110 to catch each pin 26, as shown in FIG. 9. When door 22 closes and pump activated pinch clamp 20 opens, once any other clamps on the tube that may be blocking flow are opened, fluid can flow freely.

Figure 10:
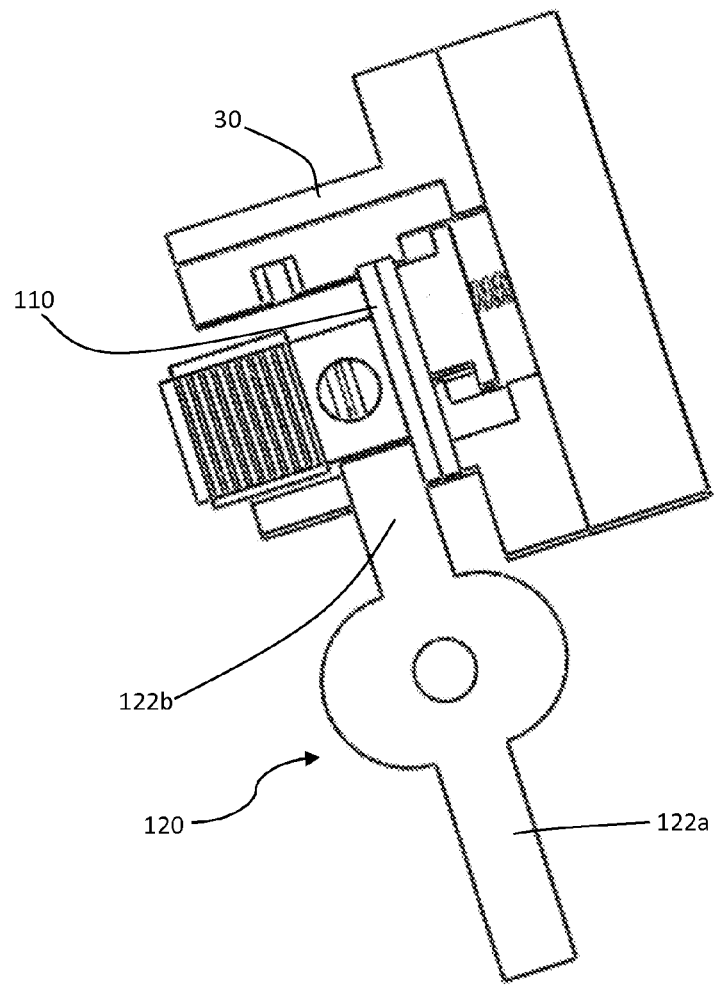
FIG. 10 is a top view of another embodiment of the pump activated pinch clamp of FIG. 9 as it is inserted in the clamp holding device and opened by a pivoting member that is activated by the closing of the door.

Other schemes to apply force on longer leg 38 of pump activated pinch clamp 20 can be used, such as rotating element 120, as shown in FIG. 10. In this scheme rotating element 120 has two arms 122a, 122b. When pump door 22 is closed pins 26 mounted on door 22 press on arm 122a of rotating element 120 causing it to rotate clockwise. Arm 122b now pushes against tab 110 connected to longer leg 38 of pump activated pinch clamp 20, opening latch 80 and opening pump activated pinch clamp 20, allowing fluid to flow freely. When door 22 is opened, pins 26 withdraw so springs 94 push spring loaded block 28 to now push longer leg 38 back toward shorter leg 36, latching pump activated pinch clamp 20 and closing off flow. Spring loaded block 28 also presses on arm 122b of rotating element 120, causing arm 122b to rotate counterclockwise back to its original position.

In one embodiment, tab 110 includes a region that extends in front of sensor 130, such as an optical sensor, to allow detection that pump activated pinch clamp 20 is present in clamp holding device 30. Sensor 130 can be included and positioned on pump housing 104 so that a portion of pump activated pinch clamp 20, such as tab 110, can activate position sensor 130 for indicating whether pump activated pinch clamp 20 is in open position 34 or closed position 32, as shown in FIG. 9. Alternatively, position sensor 130 can be elsewhere located to detect presence or position of another feature of pump activated pinch clamp 20. The sensor can be a magnet sensor and each pump activated pinch clamp can include a magnet on tab 110 or elsewhere on longer leg 38. With the sensor connected to have its data read and shown on pump display 132, the operator can know that the clamp is positioned properly inside the pump. A wire (not shown) connects position sensor 130 or the magnet sensor to a sensor circuit board (not shown) that is also on pump housing 104.

Clamp holding device 30 and spring loaded block 28 are each machined from a durable material, such as a metal, for example, stainless steel, aluminum, or brass. Alternatively, a ceramic or injection molded plastic can be used for these parts.

Clamp holding device 30 may be located adjacent top 140 of infusion pump 24 so it is easily accessed from above, as shown in FIGS. 1a and 7b. Alternatively, for situations where access is from below, it may be located near bottom 142 of infusion pump 24. Since the tubing is flexible, the tube path through infusion pump 24 can be curved. In yet another alternative, clamp holding device 30 can be located along a side of the pump. Clamp holding device can be oriented so pump activated pinch clamp 20 enters from above, below, or from the side. Pump activated pinch clamp 20 can be oriented so shorter leg 36 of the clamp is facing door 22, facing away from door 22, or facing sideways with respect to door 22.

Handling block 150 enables easy handling of pump activated pinch clamp 20 during insertion into and removal from clamp holding device 30, and is provided on longer leg 38, as shown in FIGS. 1b, 2b, 3a-3b, 4, 5a, 7a-7b, and 9. In one embodiment handling block 150 includes rough surface 88a where each finger might touch handling block 150, such as on each of the two sides and on the top surface, as shown in FIG. 9. Rough surface 88a may be lines in the plastic, and such lines may be formed during injection molding.

Alternatively, handling block 150 and tab 110 can be merged into one merged handling block structure on longer leg 38 of pump activated pinch clamp 151, as shown in open position in FIGS. 11a-11b and in closed position in FIG. 11c. In one embodiment, pin 26 mounted on door 22 presses on front face 152 of merged handling block 154 when door 22 is closed tilting longer leg 36 and opening latch 80. The pin pressure on merged handling block 154 when door 22 closes pushes pump activated pinch clamp 20 into its open position against the force of spring loaded block 28, pinching region 82 opens, and fluid flow in the tube passing through clamp 151 is no longer blocked by pump activated pinch clamp 151. When door 22 is opened pressure from pins 26 is removed and the force of spring loaded block 28 causes pump activated pinch clamp 151 and latch 80 to close, pinching the tube in pinching region 82.

Pump activated pinch clamp 151, with its hollowed out merged handling block 154 and hollowed out pinching region 82 saves material and may be easier to mold from plastic than the version shown in FIGS. 3a, 3b.

An embodiment showing components using pump activated pinch clamp 151 is illustrated in FIGS. 12-20. In this embodiment, clamp holder 160 includes wing holding slots 162 for holding wings 48 of pump activated pinch clamp 151, as shown in FIG. 13a. Clamp holder 160 also includes lever holding slot 164 for holding pivoting end 166 of lever 168, as shown in FIG. 13b. Clamp holder 160 also includes four mounting holes 170 for screws to hold clamp holder 160 to front panel 176 of pump housing 104 over opening 178, as shown in FIG. 13c.

Figure 12:
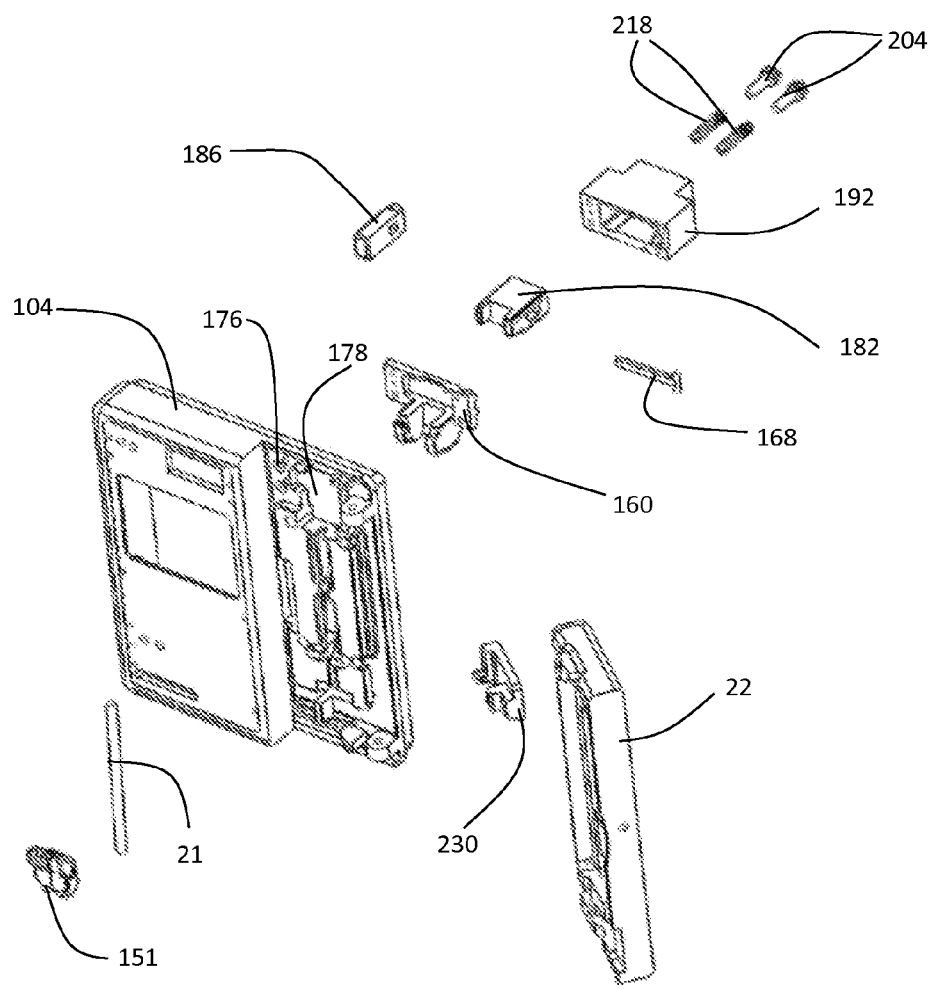
FIG. 12 is an exploded view of the pump activated pinch clamp of FIGS. 11a-11c, the infusion pump, and parts used to open and close the pump activated pinch clamp when the pump door is closed or opened.
Figure 13A:
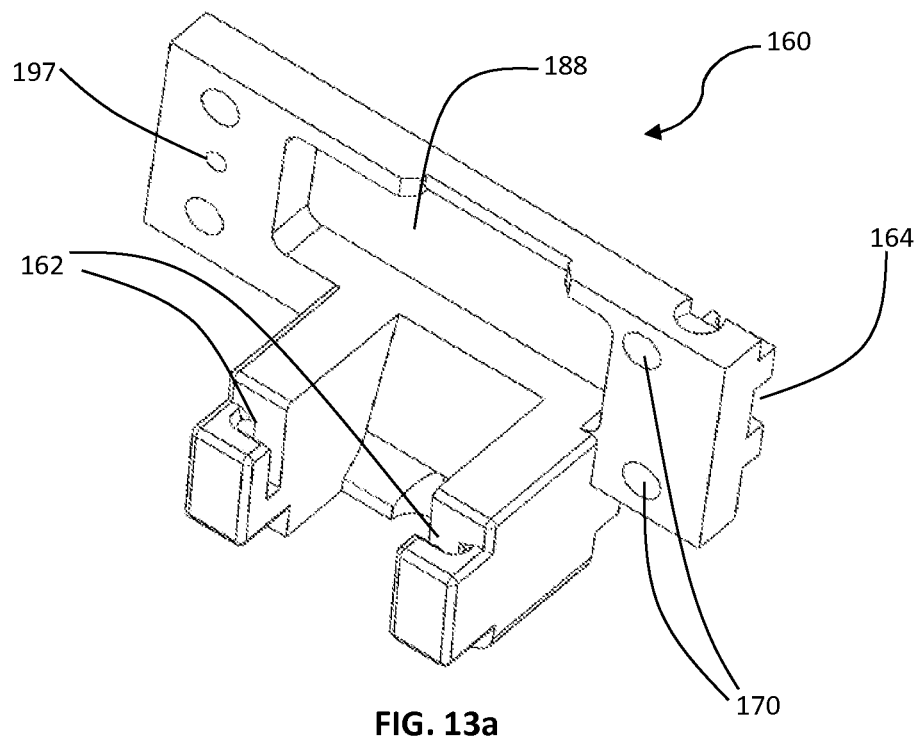
FIG. 13a is a three dimensional view of a clamp holder for holding the pump activated pinch clamp of FIGS. 11a-11c.
Figure 13B:
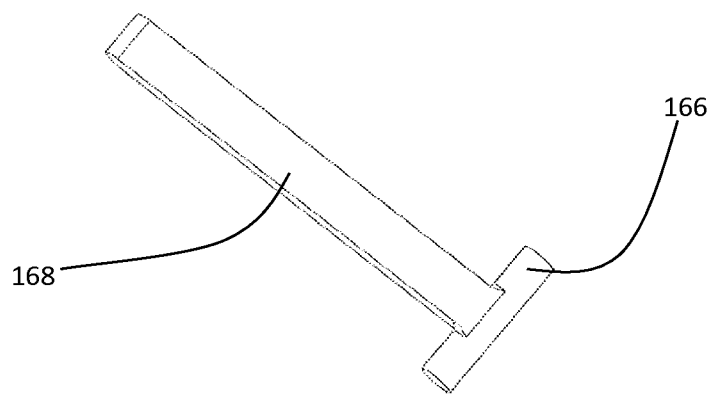
FIG. 13b is a three dimensional view of a lever for operating parts for opening the pump activated pinch clamp of FIGS. 11a-11c when the pump door is closed.

Lever 168 extends through clamp block slot 180 of clamp block 182 and through straight block slot 184 of straight block 186, as shown in FIGS. 13d-13e. Clamp block 182 and straight block 186 extend through clamp holder opening 188, as shown in FIGS. 12 and 13a.

Figure 14A:
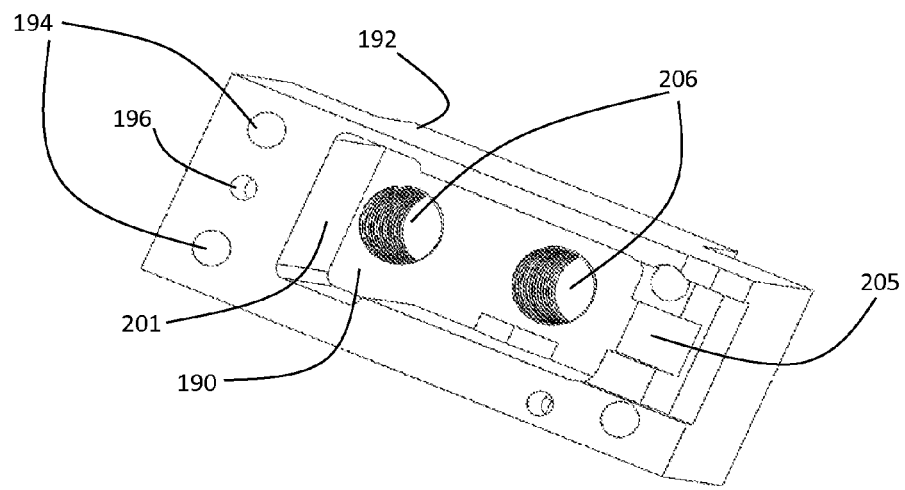
FIG. 14a is a three dimensional view of a spring housing that springably holds the clamp block and straight block of FIGS. 13d-13e.
Figure 14B:
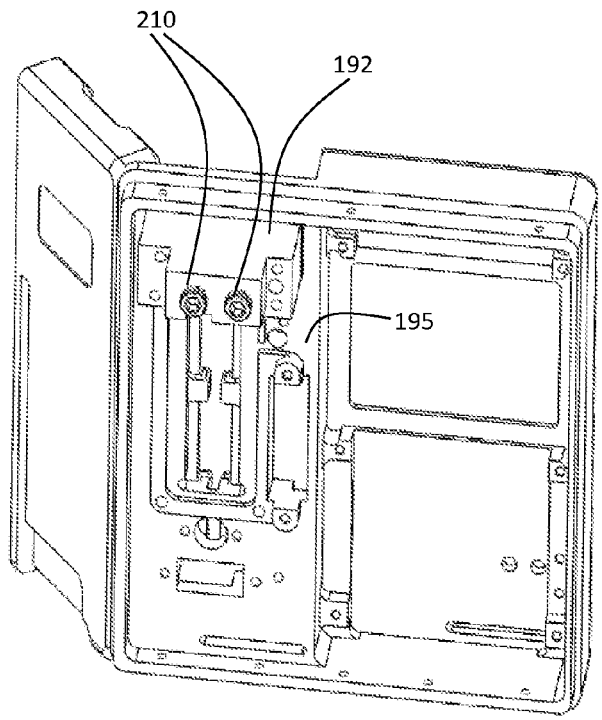

Clamp block 182 and straight block 186 fit into chamber 190 of spring housing 192, as shown in FIG. 14a. Spring housing 192 includes four spring housing clearance holes 194 that align with clamp holder mounting holes 170 and with holes on front panel 176 for screw mounting spring housing 192 and clamp holder 160 to back surface 195 of front panel 176, as shown in FIG. 14b. Nuts are used behind spring housing 192 to hold the four screws. Before connection to front panel 176, spring housing 192 is connected to clamp holder 160 with a screw (not shown) that extends through hole 196 in spring housing 192 and hole 197 in clamp holder 160. Straight block 186 also includes surface 198 and extensions 200. Extensions 200 fit into enlarged area 201 of spring housing 192. Clamp block 182 also includes protrusions 202 and surface 204 there between. Spring housing 192 includes cut out section 205 for lever 168, as shown in FIG. 14a.

Figures 14C, 14D:
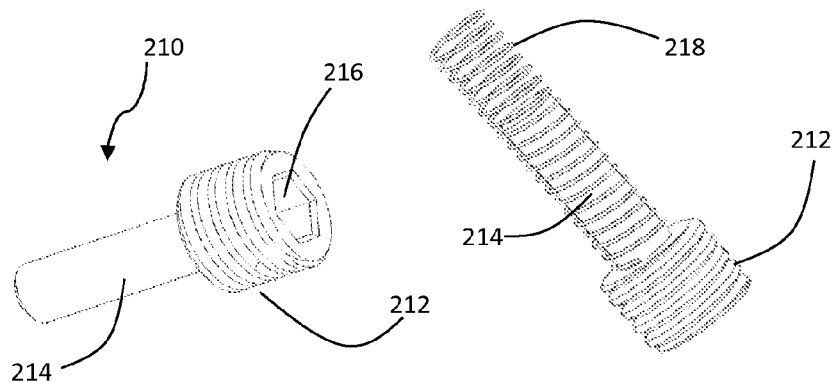
FIGS. 14c and 14d are three dimensional views of a screw and a screw mounted spring that springably holds the clamp block and straight block in the spring housing of FIGS. 14a-14b.

Spring housing 192 also includes threaded through holes 206 for holding screw 210 that has threaded head 212 and unthreaded tail 214, as shown in FIGS. 14b-14d. Screw 210 has hexagonal slot 216, allowing turning screw 210 with an allen wrench. Hexagonal slot 216 and threaded head 212 allows adjusting position of screw 210 in threaded through holes 206, allowing adjusting initial loading of spring 218. Unthreaded tail 214 holds spring 218.

Figure 14E:
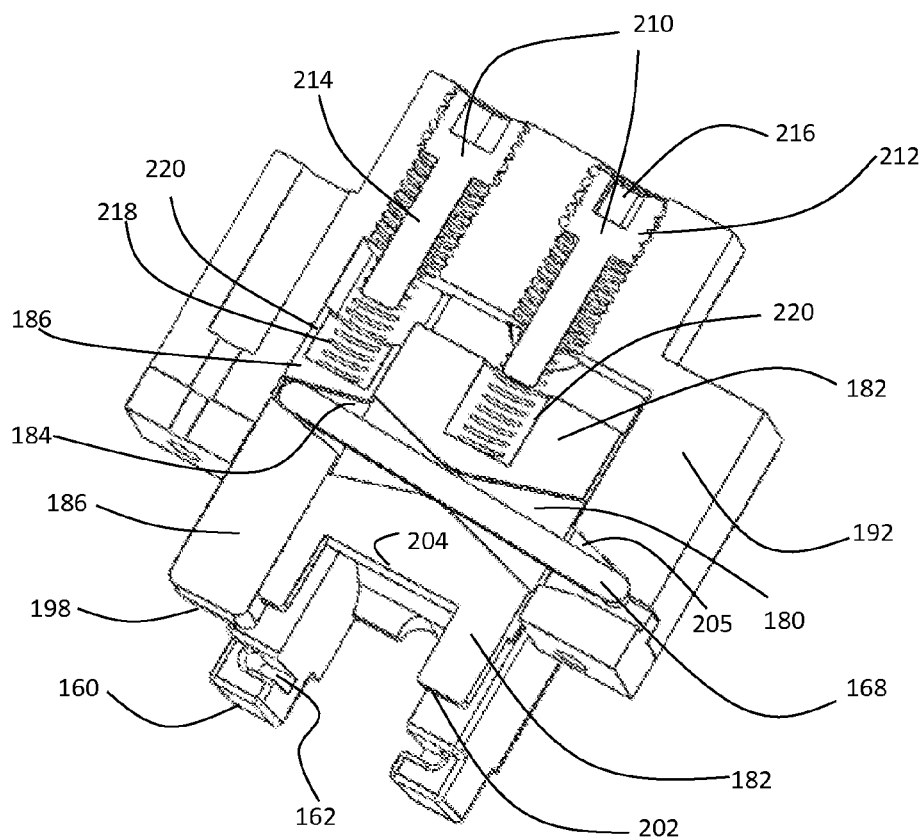
FIG. 14e is a cross sectional view of the assembly including the clamp holder of FIG. 13a, the lever of FIG. 13b, the clamp block of FIG. 13d, the straight block of FIG. 13e, the spring housing of FIG. 14a, the screws of FIGS. 14c and 14d, and the springs of FIG. 14d.

Assembly of clamp holder 160, clamp block 182, straight block 186, lever 168, spring housing 192, screws 210, and spring 218 are shown in cross section in FIG. 14e. Slot 180 in clamp block 182 and slot 184 in straight block 186 and blind holes 220 for springs 218 in clamp block 182 and straight block 186 are visible in the cross section.

Figure 15A:
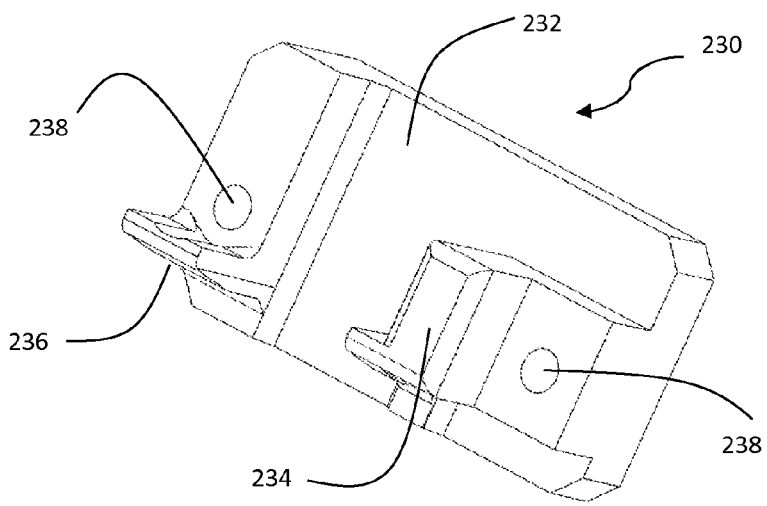
FIG. 15a is a three dimensional view of a door block that pushes on the clamp head of FIG. 11c and on the straight block of FIG. 13e when the pump door is closed causing the clamp to open.
Figure 15B:
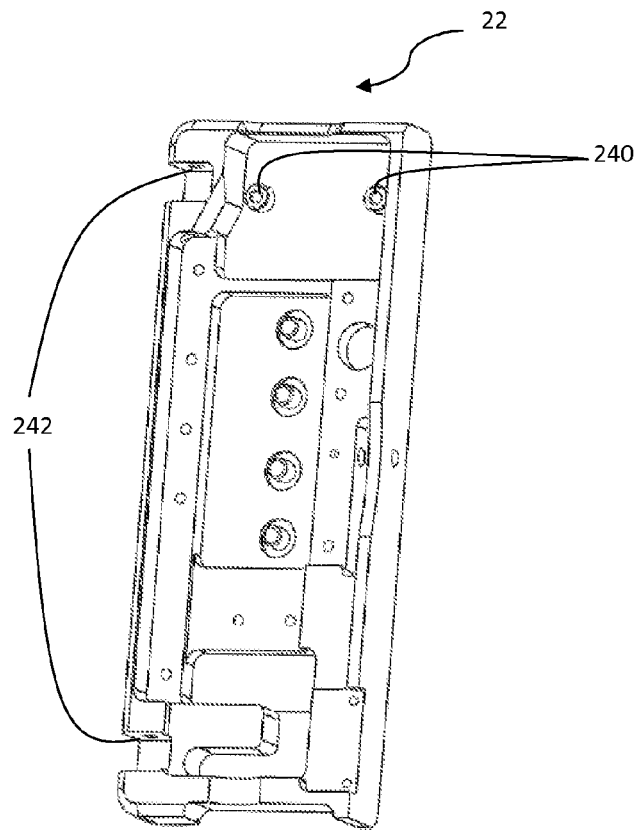
Figure 16:
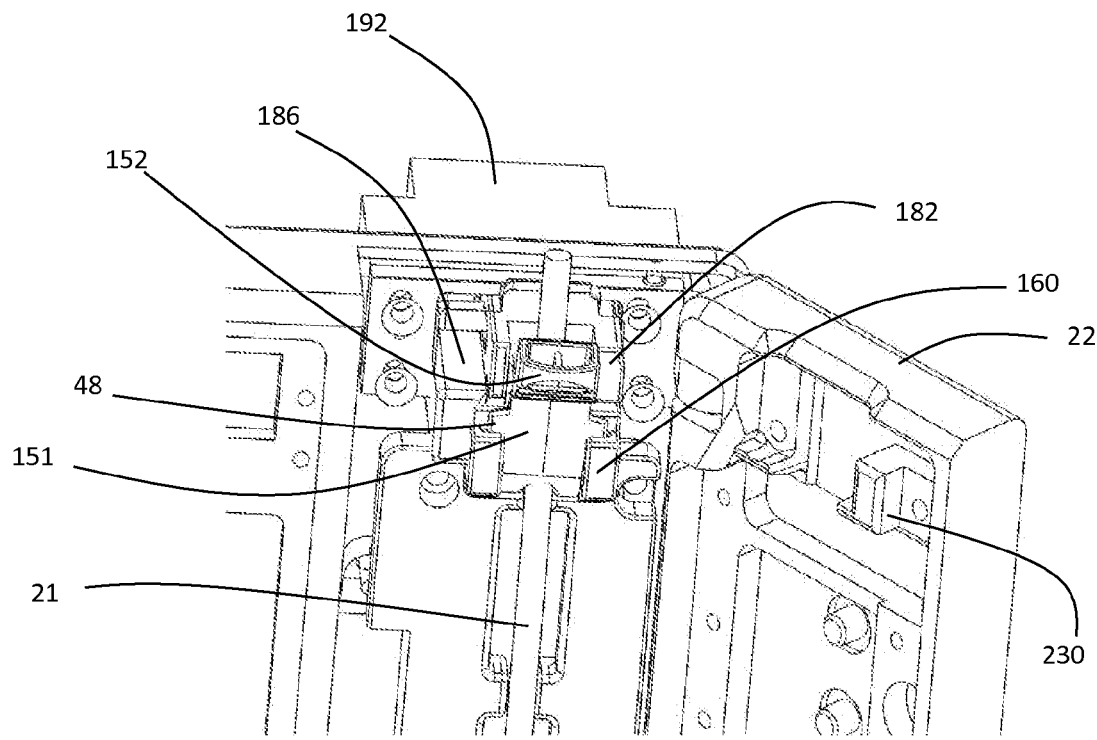
FIG. 16 is a three dimensional view of part of an infusion pump housing showing the pinch clamp installed in the clamp holder and the door block installed on the door.

In this embodiment door block 230 is mounted to pump door 22, as shown in FIGS. 15a-15b and FIG. 16. Door block 230 includes surface 232 that pushes on front face 152 of merged handling block 154 when door 22 is closed, thereby opening pump activated pinch clamp 151.

Door block 230 also includes protrusion 234 that is aligned to press on surface 196 of straight block 186 pushing straight block 186 back against spring 218 when pump door 22 is closed. Because lever 168 is inserted through straight block slot 184 of straight block 186, when straight block 186 is pushed back, lever 168 is also pushed back, and because lever 168 also extends through clamp block slot 180 of clamp block 182, this movement of lever 168 drives clamp block 182 back as well. Thus closing pump door 22 drives clamp block 182 back giving pump activated pinch clamp 151 room to open without interference from clamp block 182.

Door block 230 also includes protrusion 236 that is aligned to extend over wing 48, as shown in FIGS. 15a and 16 so pump activated pinch clamp 151 is restricted from moving up when front face 152 of merged handling block 154 is pushed by surface 232 of door block 230.

Door block 230 also includes mounting holes 238 for mounting door block 230 to threaded mounting holes 240 in door 22, as shown in FIG. 15b. Door 22 also has door hinges 242 to assemble door 22 with pump front panel 176.

Figures 1C, 1D:
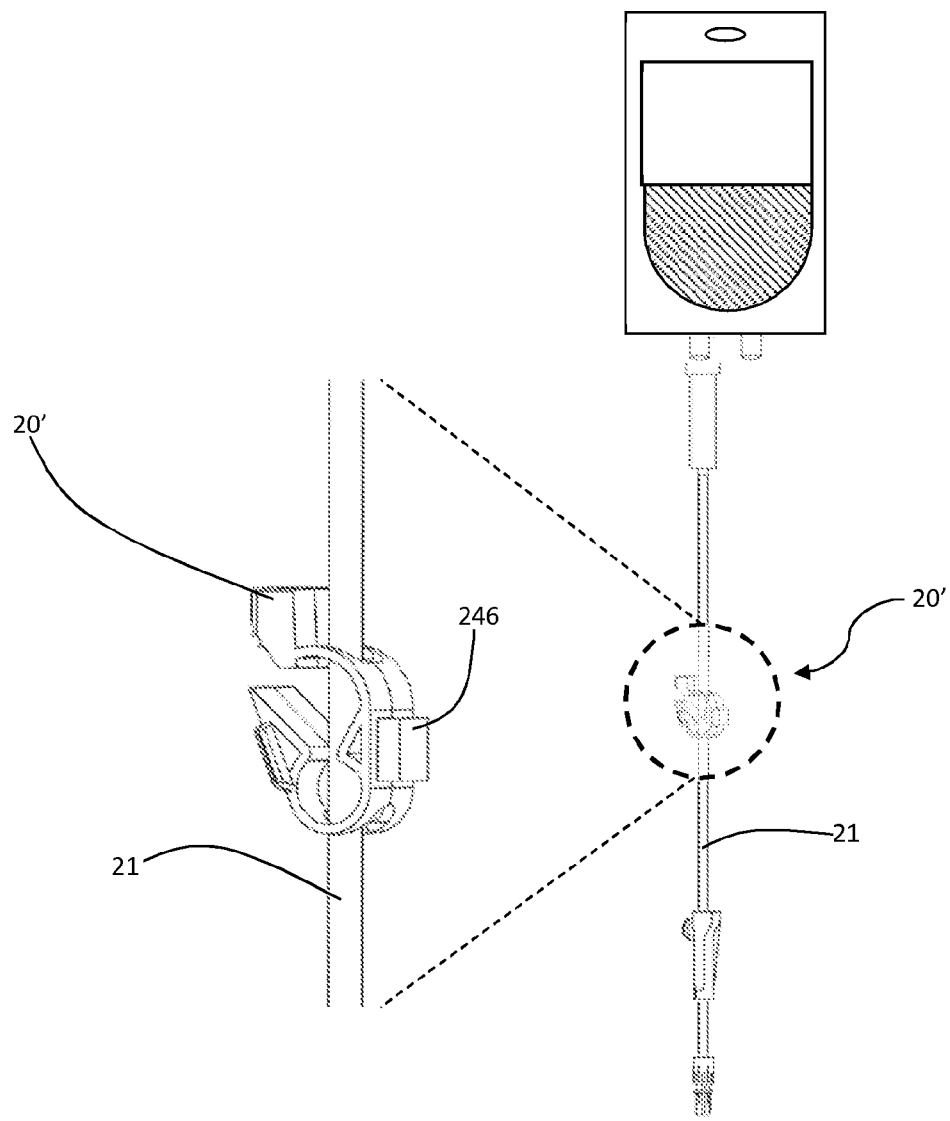
FIG. 1c is a front view of the pump activated pinch clamp of FIG. 1b connected to tubing and to a container holding the medication for the infusion.
FIG. 1d is an enlarged three dimensional view of the pump activated pinch clamp and tubing of FIG. 1c showing a bar code or memory device mounted to the pump activated pinch clamp.

In another embodiment, information containing structure 246, such as a bar code or a memory containing device, such as an RFID tag or a USB device, is attached to the pump activated pinch clamp by the pharmacist supplier, as shown in FIG. 1c. The pharmacist can provide the bar code or memory containing device with information about the patient and about the container that the tubing and the pump activated pinch clamp are connected to. The information may include drug name, dose, dose rate, name of patient, patient ID number, and other pharmacist notes. A USB device on the pinch clamp can be plugged into a socket on the pump when the pinch clamp is mounted. A reader mounted on the pump may be connected to read this information from the memory containing device. The information can also be provided on display 132. The health practioner can compare the patient name on the screen with the name of the patient on the wrist band and can set pump controls to ensure that she sets the pump to provide the correct dose of the proper infusion medication to the correct patient at the correct dose rate. In another embodiment, a microprocessor in the pump is connected to use the information received by the reader to automatically set pump parameters, including dose and dose rate.

In another embodiment, the pump includes a bar code reader to read a bar code on the wrist band of the patient (not shown) and automatically compares the patient information on the wrist band with the patient information on the RFID tag or USB device mounted on the clamp to ensure that the correct patient is being infused with the correct medication. Alternatively, if the wrist band includes another RFID tag, the pump can use its RFID tag reader to read both the wrist band RFID tag and the RFID tag mounted on the clamp for this purpose.

Information read from information containing structure 246 can be used for confirming that the correct patient is getting the correct drug. The confirmation may be by the care giver comparing readings from the pump display with the patient's wrist band. The confirmation may be by pump itself, for example, by the pump reading information from both the clamp and from the wrist band. If the patient ID does not match, the microprocessor would cause the alarm to ring. If the information matches, the display would provide a confirmation message.

Passive RFID tags, such as part number 32398 from Parallax, Inc. or active RFID tags, such as part number 28147 from Parallax can be used. RFID readers and writers, including passive RFID reader part number 28440 from Parallax and active RFID reader and writer part number GAO241026 from GAO RFID Inc. can be used. Information can be stored on such non-volatile memory as EEPROM part number AT24C64C from Microchip or on a USB drive, such as Texas Instruments part number OMAP3440.

Figure 17A:
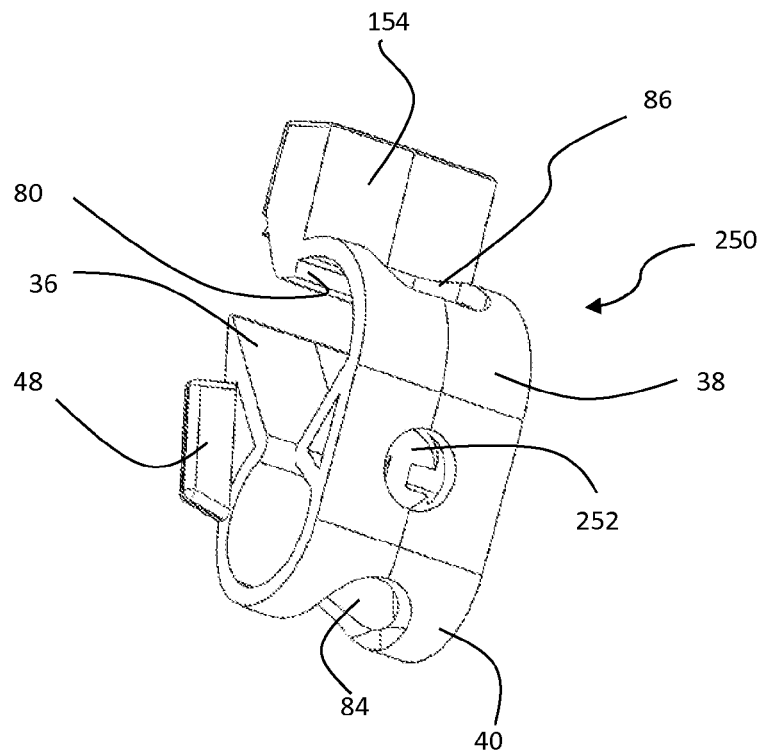
FIG. 17a is a three dimensional view of another embodiment of a pump activated pinch clamp in the open position with a slot to install a magnet.
Figure 17B:
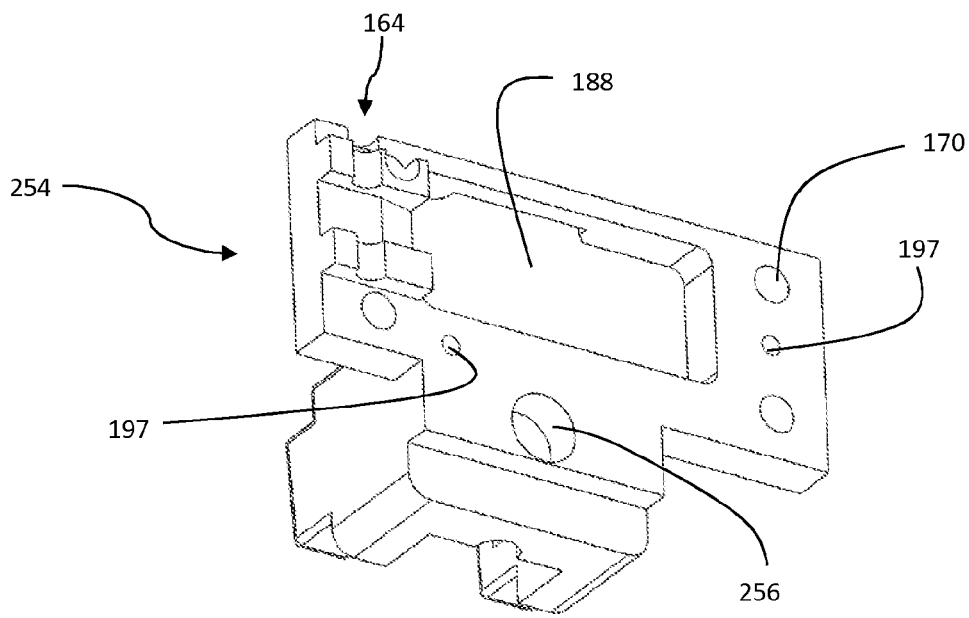
Figure 17C:
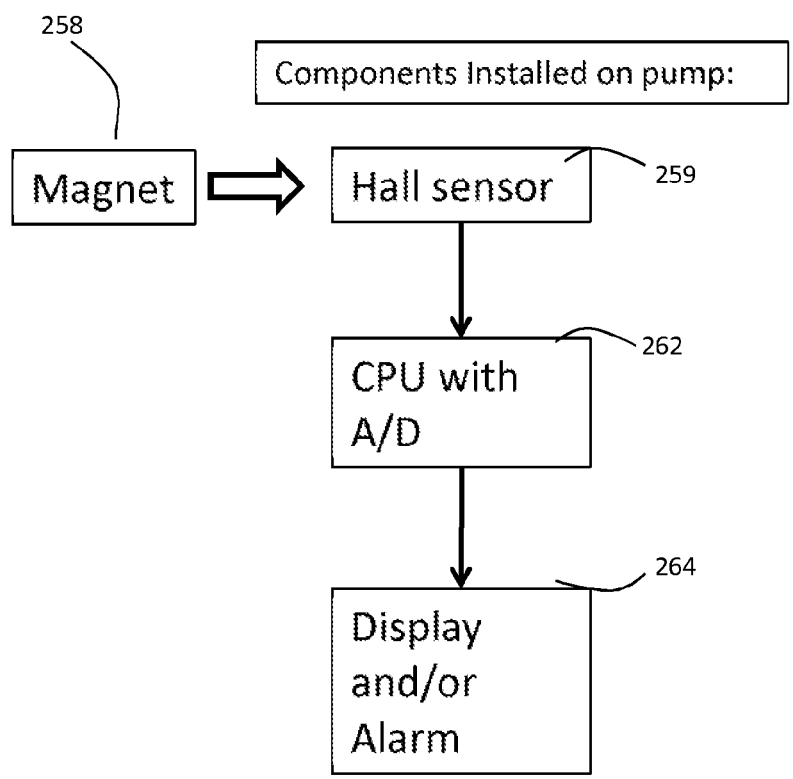
FIG. 17c is a block diagram of showing interaction between magnet and hall sensor and interconnections between hall sensor, microprocessor, and display for the embodiment of FIGS. 17a-17b.

In another embodiment, pump activated pinch clamp 250 includes slot 252 to install a magnet, as shown in FIG. 17a. Clamp holder 254 includes slot 256 to install a sensor to detect the magnetic field of the magnet, as shown in FIG. 17b. The sensor can be a hall sensor. A block diagram showing the interaction of magnet 258 on pump activated pinch clamp 250 with hall sensor 259 on clamp holder 254 and the output of hall sensor 259 being received by analog to digital converter and microprocessor 262 which provides an output to display 264 indicating the presence of pump activated pinch clamp 250 in position in clamp holder 254 of the pump is shown in FIG. 17c. An alarm can also be used. As longer leg 38 of pump activated pinch clamp 250 moves toward hall sensor 259 when pump activated pinch clamp 250 is opened and as longer leg 38 of pump activated pinch clamp 250 moves away from hall sensor 259 when pump activated pinch clamp 250 is closed, hall sensor will provide different outputs depending on whether pump activated pinch clamp 250 is absent, closed, or open. Thus, the operator can verify that pump activated pinch clamp 250 is in place and that pump activated pinch clamp 250 is in its open or in its closed position.

While the disclosed methods and systems have been shown and described in connection with illustrated embodiments, various changes may be made therein without departing from the spirit and scope of the invention as defined in the appended claims.

What is claimed is:

1. A system for controlling flow of a fluid in a tube with a controlling device, comprising a pinch clamp, wherein said pinch clamp has a first leg, a second leg, a connecting region there between, and a pinching region, wherein said first leg and said second leg are both connected to said connecting region, wherein whether said pinching region is in an open position, for allowing flow of the fluid, or in a closed position, for preventing flow of the fluid, is determined by spacing between said first leg and said second leg, wherein said first leg includes a first latching element and wherein said second leg includes a second latching element, wherein said first latching element is latched with said second latching element when said pinch clamp is in said closed position and wherein said first latching element is not latched with said second latching element when said pinch clamp is in said open position, wherein said first leg includes a first part of a quick release connector, wherein said first part of said quick release connector includes an element for quickly mounting said pinch clamp to the controlling device and for quickly dismounting said pinch clamp from the controlling device.

2. A system as recited in claim 1, further comprising said controlling device, wherein said controlling device includes a pinch clamp holding device, wherein said pinch clamp holding device includes a second part of said quick release connector, wherein said first part of said quick release connector mates with said second part of said quick release connector for holding said first leg of said pinch clamp in said pinch clamp holding device.

3. A system as recited in claim 2, further comprising a first quick release latching element on said first part of said quick release connector and a second quick release latching element on said second part of said quick release connector for quick releasably latching said first part of said quick release connector with said second part of said quick release connector.

4. A system as recited in claim 2, wherein said controlling device further comprises a second leg positioning device for determining position of said second leg when said first leg is held in said pinch clamp holding device.

5. A system as recited in claim 4, wherein said second leg positioning device includes a first forcing element, wherein said first forcing element is adjacent said second leg when said pinch clamp is in said clamp holding device, wherein operation of said first forcing element automatically forces said second leg to provide said pinch clamp in its closed position or retains said pinch clamp in its closed position when said pinch clamp is inserted into said clamp holding device.

6. A system as recited in claim 5, wherein said controlling device further includes a second forcing element, wherein said second leg includes a pressing region, wherein said second forcing element is positioned to push on said pressing region to press said second leg away from said held first leg to provide said pinch clamp in its open position.

7. A system as recited in claim 6, wherein said controlling device includes a controlling device door, wherein said controlling device door includes said second forcing element wherein said second forcing element is positioned to push on said pressing region when said controlling device door is closed.

8. A system as recited in claim 7, wherein the controlling device includes a third forcing element, wherein said third forcing device is connected to said first forcing element, wherein said second forcing element is positioned to push said third forcing element when said door is closed, wherein said pushing said third forcing element moves said first forcing device away from said second leg, providing room for said second leg to be pushed away from said first leg when said second forcing element presses on said pressing region.

9. A system as recited in claim 6, wherein operation of said first forcing element latches said first latching element with said second latching element, and wherein operation of said second forcing element unlatches said first latching element from said second latching element.

10. A system as recited in claim 1, wherein said first part of said quick release connector includes a wing region, wherein said connecting region has a connecting region width, wherein said wing region has a wing region width, wherein said wing region width is larger than said connecting region width.

11. A system as recited in claim 10, wherein said wing region includes a first wing and a second wing, wherein said connecting region has a first edge and a second edge, wherein said first wing extends beyond said first edge and wherein said second wing extends beyond said second edge.

12. A system as recited in claim 11, wherein said first wing includes a first extension and wherein said second wing includes a second extension.

13. A system as recited in claim 12, wherein said first extension includes a first quick release latching element.

14. A system as recited in claim 10, further comprising a pinch clamp holding device, wherein said pinch clamp holding device includes a slot for holding said wing region and said first leg in a fixed position when said pinch clamp is in said clamp holding device.

15. A system as recited in claim 1, wherein said second leg includes a handling block, wherein said handling block has a surface, wherein pushing said surface causes said pinching region to move to said open position.

16. A system as recited in claim 1, wherein said pinch clamp includes a rough surface.

17. A system as recited in claim 1, wherein the controlling device is an infusion pump for providing the fluid to a patient, wherein said pinch clamp includes an information containing structure containing at least one from the group consisting of information about the patient, information about the fluid, and instruction about dispensing the fluid.

18. A system as recited in claim 17, wherein said information containing structure includes one from the group consisting of a bar code and a memory containing device.

19. A system as recited in claim 17, wherein said memory containing device includes one from the group consisting of an RFID tag and a USB memory.

20. A system as recited in claim 17, further comprising the infusion pump, wherein the infusion pump includes a reader for reading information on said information containing structure.

21. A system as recited in claim 20, wherein the infusion pump includes a display for displaying information in the information containing structure.

22. A system as recited in claim 20, wherein the infusion pump includes a processor, wherein said processor provides an output to said display indicating confirmation of said information based on information in said information containing structure.

23. A system as recited in claim 1, wherein the controlling device is an infusion pump for providing the fluid to a patient, wherein said infusion pump includes a pinch clamp holding device, wherein said pinch clamp holding device includes a second part of said quick release connector, wherein said first part of said quick release connector mates with said second part of said quick release connector for holding said first leg of said pinch clamp in a fixed position in said pinch clamp holding device, wherein said infusion pump further comprises a second leg positioning device for determining position of said second leg when said first leg is connected with said pinch clamp holding device, wherein said second leg positioning device includes a first forcing element, wherein said first forcing element is adjacent said second leg when said pinch clamp is in said clamp holding device, wherein operation of said first forcing element automatically forces said second leg to provide said pinch clamp in its closed position or retains said pinch clamp in its closed position when said pinch clamp is inserted into said clamp holding device, wherein said infusion pump further includes a second forcing element, wherein said second leg includes a pressing region, wherein said second forcing element is positioned to push on said pressing region to press said second leg away from said fixed first leg to provide said pinch clamp in its open position, wherein said infusion pump includes an infusion pump door, wherein said infusion pump door includes said second forcing element, wherein said second forcing element is positioned to push on said pressing region when said infusion pump door is closed.

24. A system, comprising a pinch clamp, a tube for providing a fluid, and a control housing, wherein said pinch clamp is mounted on said tube for controlling flow of the fluid, wherein said tube and said pinch clamp are for fitting in said control housing, wherein said pinch clamp has a closed position and an open position, wherein when said pinch clamp is in said closed position flow of the fluid is prevented and when said pinch clamp is in said open position the fluid can flow in the tube, wherein said pinch clamp includes a first leg, and a second leg, wherein said first leg includes a first latching element and wherein said second leg includes a second latching element, wherein said first latching element is latched with said second latching element when said pinch clamp is in said closed position and wherein said first latching element is not latched with said second latching element when said pinch clamp is in said open position, wherein said control housing includes a first force applying device and a second force applying device, wherein said first force applying device automatically forces said pinch clamp into said closed position and wherein said second force applying device counters said first force applying device and automatically forces said pinch clamp into said open position, wherein said second force applying device is different from said first force applying device.

25. A system as recited in claim 24, wherein said control housing includes a door, wherein said door has an open position and a closed position, wherein said second force applying device is connected to said door, wherein said second force applying device operates to force said pinch clamp into said open position when said door is closed and wherein said second force applying device does not operate to force said pinch clamp into said open position when said door is open, wherein said first force applying element forces said pinch clamp into said closed position when said door is open.

26. A system as recited in claim 24, wherein operation of said first force applying device latches said first latching element with said second latching element and wherein operation of said second force applying device unlatches said first latching element from said second latching element.

27. A system as recited in claim 24, wherein said control housing includes a clamp holding device for holding said first leg in a fixed position, wherein said first force applying device includes a spring loaded device, wherein said spring loaded device operates on said second leg to force said second leg toward said first leg to place said pinch clamp in closed position.

28. A system as recited in claim 24, wherein said pinch clamp includes a connecting region, wherein said first leg and said second leg join in said connecting region, wherein said first leg includes a wing region, wherein said wing region protrudes beyond an edge of said connecting region, wherein said clamp holding device includes a slot for holding said wing region.

29. A system as recited in claim 24, wherein said second leg includes a handling block, wherein said handling block has a surface, wherein pushing said surface causes said pinching region to move to said open position.

30. A system as recited in claim 29, wherein said second force applying device is aligned to operate on said handling block.

31. A system as recited in claim 24, wherein said control housing includes a pump for pumping the fluid.

32. A system as recited in claim 31, wherein said pump includes a peristaltic pump.

33. A system as recited in claim 24, wherein said pinch clamp is permanently connected to said tube.

34. A system as recited in claim 24, wherein said pump housing further includes a sensor, wherein said sensor is positioned to determine presence of said clamp in said clamp holding device.

35. A system as recited in claim 34, wherein said sensor is positioned to determine whether said clamp is in an open position or in a closed position.

36. A method of operating a pump for pumping a fluid, comprising:

a. providing the pump, wherein the pump includes a pump housing, a door, and a clamp holding device, wherein said clamp holding device includes a first forcing element and wherein said door includes a second forcing element;

b. providing a tube and a clamp, wherein said clamp has a first leg and a second leg, and wherein said clamp has an open position and a closed position, wherein when said clamp is in said open position said clamp does not prevent fluid flow and wherein when said clamp is in said closed position fluid cannot flow, wherein said first leg includes a first latching element and wherein said second leg includes a second latching element, wherein said first latching element is latched with said second latching element when said clamp is in said closed position and wherein said first latching element is not latched with said second latching element when said clamp is in said open position;

c. inserting said first leg into said clamp holding device, wherein when said clamp holding device holds said first leg, wherein when said door is open said first forcing element acts to force said clamp to be in a closed position; and d. closing said door, wherein said door closing activates said second forcing element, wherein said second forcing element acts to force said clamp to be in said open position.

37. A system, comprising a pinch clamp and a clamp holding device, wherein said pinch clamp has an open position and a closed position, wherein said pinch clamp has a first leg and a second leg, wherein said first leg includes a first connecting element and wherein said second leg includes a second connecting element, wherein said first connecting element is connected with said second connecting element when said clamp is in said closed position and wherein said first connecting element is not connected with said second connecting element when said clamp is in said open position, wherein said first leg includes a first part of a quick release connector and wherein said clamp holding device includes a second part of said quick release connector, wherein said second part of said quick release connector is for holding said first part of said quick release connector.

38. A system for controlling flow of a fluid in a tube for operation with a pinch clamp holding device having a slot, comprising a pinch clamp and a control housing, wherein said pinch clamp includes a first leg, a second leg, a connecting region there between, and a pinching region, wherein said pinch clamp has a closed position and an open position, wherein when said pinch clamp is in said closed position flow of the fluid is prevented and when said pinch clamp is in said open position the fluid can flow in the tube, wherein said second leg is moveable toward said first leg to prevent fluid flow in the tube through said pinching region, and wherein said second leg is moveable away from said first leg to allow fluid flow in the tube through said pinching region, wherein said first leg includes a quick release element shaped for quickly slideably mounting into the slot in the pinch clamp holding device and for quickly slideably dismounting from the slot in the pinch clamp holding device, wherein said control housing includes a first force applying device and a second force applying device, wherein said first force applying device automatically forces said pinch clamp into said closed position and wherein said second force applying device counters said first force applying device and automatically forces said pinch clamp into said open position, wherein said second force applying device is different from said first force applying device.

39. A system as recited in claim 38, wherein said connecting region has a connecting region width, wherein said element has an element width, wherein said element width is larger than said connecting region width.

40. A system as recited in claim 39, wherein said element includes a first wing and a second wing, wherein said connecting region has a first edge and a second edge, wherein said first wing extends beyond said first edge and wherein said second wing extends beyond said second edge.

41. A system as recited in claim 34, wherein said sensor includes an optical sensor.

* * * * *